United States Patent
Limburg

(10) Patent No.: US 12,272,104 B2
(45) Date of Patent: Apr. 8, 2025

(54) METHOD AND DEVICES FOR PERFORMING AN ANALYTICAL MEASUREMENT

(71) Applicant: Roche Diabetes Care, Inc., Indianapolis, IN (US)

(72) Inventor: Bernhard Limburg, Soergenloch (DE)

(73) Assignee: Roche Diabetes Care, Inc, Indianapolis, IN (US)

(*) Notice: Subject to any disclaimer, the term of this patent is extended or adjusted under 35 U.S.C. 154(b) by 1044 days.

(21) Appl. No.: 16/991,917

(22) Filed: Aug. 12, 2020

(65) Prior Publication Data

US 2020/0372680 A1 Nov. 26, 2020

Related U.S. Application Data

(63) Continuation of application No. PCT/EP2019/053993, filed on Feb. 18, 2019.

(30) Foreign Application Priority Data

Feb. 19, 2018 (EP) ...................................... 18157426

(51) Int. Cl.
*G06T 7/90* (2017.01)
*G01N 21/78* (2006.01)
(Continued)

(52) U.S. Cl.
CPC .............. *G06T 7/90* (2017.01); *G01N 21/78* (2013.01); *G01N 21/8483* (2013.01); *G06T 7/11* (2017.01);
(Continued)

(58) Field of Classification Search
CPC ... G06T 7/90; G06T 7/11; G06T 2207/10024; G01N 21/78; G01N 21/8483;
(Continued)

(56) References Cited

U.S. PATENT DOCUMENTS

| 5,717,778 A | * | 2/1998 | Chu | .......................... G06T 7/90 |
| | | | | 382/133 |
| 6,993,172 B2 | | 1/2006 | Connell et al. | |

(Continued)

FOREIGN PATENT DOCUMENTS

| CN | 103620392 A | 3/2014 |
| CN | 103649731 A | 3/2014 |

(Continued)

OTHER PUBLICATIONS

International Search Report and Written Opinion of the International Searching Authority, PCT/EP2019/053993, Jun. 18, 2019, 12 pages.

(Continued)

*Primary Examiner* — Matthew D Krcha
*Assistant Examiner* — Sophia Y Lyle
(74) *Attorney, Agent, or Firm* — Bose McKinney & Evans LLP

(57) ABSTRACT

A method, a mobile device and a kit for performing an analytical measurement are disclosed, wherein outliers are eliminated. In the inventive method, a mobile device having a camera and a test strip for performing a color-change detection reaction are provided. A sample is applied to a test field of the test strip and an image of at least part of the test strip is captured. A region of interest in the image is determined and associated with a first sub-set of pixels. A color distribution is evaluated and outliers are eliminated in the first sub-set of pixels. A sub-region of interest is determined within the region of interest and is associated with a second sub-set of pixels. Mean values of the color distributions of the first sub-set of pixels and the second sub-set of pixels are compared to thereby determine homogeneity information of the image.

16 Claims, 5 Drawing Sheets

(51) Int. Cl.
*G01N 21/84* (2006.01)
*G06T 7/11* (2017.01)
*A61B 5/145* (2006.01)

(52) U.S. Cl.
CPC . *A61B 5/14532* (2013.01); *G06T 2207/10024* (2013.01)

(58) Field of Classification Search
CPC ... G01N 2021/0162; G01N 2021/7759; G01N 2021/8488; G01N 2201/0221; A61B 5/14532
See application file for complete search history.

(56) References Cited

U.S. PATENT DOCUMENTS

| | | | |
|---|---|---|---|
| 9,285,323 | B2 | 3/2016 | Burg et al. |
| 2009/0116015 | A1 | 5/2009 | Petrich et al. |
| 2014/0051187 | A1* | 2/2014 | Evers ............... G01N 21/00 422/69 |
| 2014/0154789 | A1 | 6/2014 | Polwart et al. |
| 2014/0294239 | A1 | 10/2014 | Duckett |
| 2015/0111236 | A1 | 4/2015 | Dickopf |
| 2015/0254844 | A1 | 9/2015 | Tsai et al. |
| 2015/0308961 | A1* | 10/2015 | Burg ............... G01N 21/78 382/165 |
| 2016/0153912 | A1* | 6/2016 | Dickopf ............... G06T 7/32 436/95 |
| 2016/0239709 | A1* | 8/2016 | Shriver ............... G06V 20/188 |

FOREIGN PATENT DOCUMENTS

| | | | | |
|---|---|---|---|---|
| CN | 104364636 A | | 2/2015 | |
| CN | 105181959 A | | 12/2015 | |
| DE | 19630160 A1 | * | 1/1998 | ......... G01N 21/8483 |
| DE | 19638065 A1 | * | 3/1998 | ......... B28B 17/0072 |
| EP | 1 359 409 A2 | | 11/2003 | |
| JP | 2014-98645 A | | 5/2014 | |
| RU | 2014 127 535 A | | 2/2016 | |
| TW | 200424526 A | | 11/2004 | |
| TW | 201621311 A | | 6/2016 | |
| TW | 201631310 A | | 9/2016 | |
| WO | WO 2007/115732 A1 | | 10/2007 | |
| WO | WO 2014/178062 A2 | | 11/2014 | |

OTHER PUBLICATIONS

Hönes et al., Diabetes Technology and Therapeutics, vol. 10, Supplement 1, 2008, pp. 10-26.

* cited by examiner

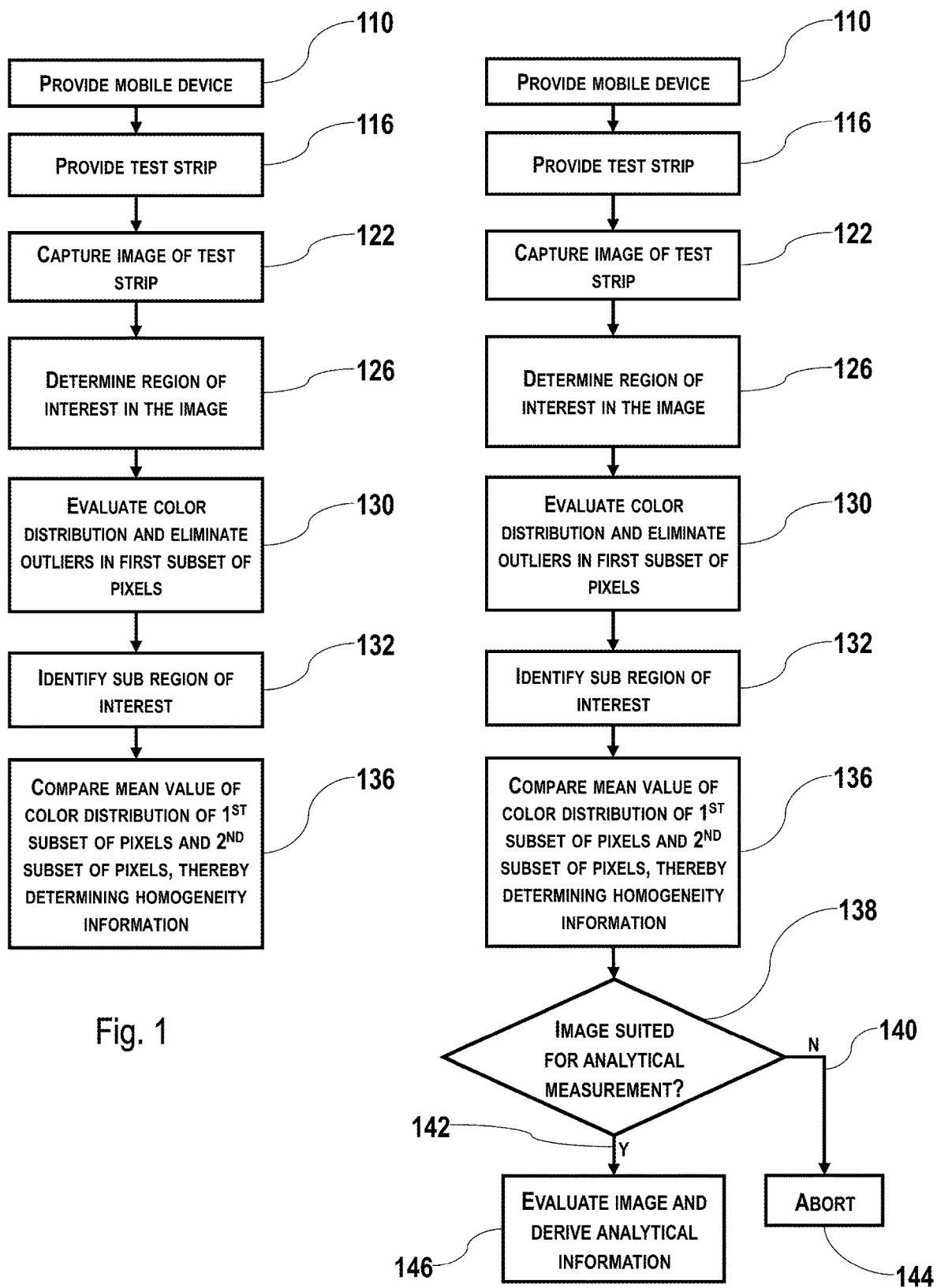

METHOD AND DEVICES FOR PERFORMING AN ANALYTICAL MEASUREMENT

RELATED APPLICATIONS

This application is a continuation of PCT/EP2019/053993, filed Feb. 18, 2019, which claims priority to EP 18 157 426.0, filed Feb. 19, 2018, the entire disclosures of which are hereby incorporated herein by reference in their entireties.

BACKGROUND

The present application refers to a method for performing an analytical measurement. This disclosure further relates to a computer program with program means for executing the method according to this disclosure. Further, this disclosure refers to a mobile device and a kit for performing an analytical measurement. Methods, computer programs, mobile devices and kits according to this disclosure may be used in medical diagnostics, in order to qualitatively or quantitatively detect one or more analytes in one or more body fluids. Other fields of application of this disclosure, however, are possible.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemistries, which, in presence of the analyte to be detected, are capable of performing one or more detectable detection reactions, such as optically detectable detection reactions. With regard to these test chemistries, reference may be made, e.g., to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing this disclosure.

Typically, one or more optically detectable changes in the test chemistry are monitored, in order to derive the concentration of the at least one analyte to be detected from these changes. For detecting the at least one change of optical properties of the test field, various types of detectors are known in the art. Thus, various types of light sources for illuminating the test fields as well as various types of detectors are known. Besides single detectors such as photodiodes, various types of devices using detector arrays having a plurality of photosensitive devices are known. Thus, WO 2007/115732 A1 discloses a system for determining the concentration of an analyte in a liquid sample. The system comprises a detection unit for detecting light intensities, which are radiated from partial regions of a detection region of a test element. The system further comprises an evaluation unit which determines a frequency distribution for the detected light intensities. Similarly, EP 1 359 409 A2 discloses an apparatus for determining the concentration of an analyte in a physiological sample. The apparatus includes at least one light source and a detector array.

Further, when using detector arrays, methods are known in the art for detecting errors and artifacts in the images acquired by the detector arrays. Thus, EP 1 359 409 A2 discloses means for determining whether a sufficient amount of sample is present on each of a plurality of different detector areas, wherein only light detected from those areas determined to have sufficient sample is used for determining the concentration of the analyte. Similarly, in WO 2007/115732 A1 the evaluation unit determines the concentration of the analyte from a light intensity selected on the basis of the frequency distribution, wherein the frequency distribution has at least one first maximum, which is caused by unwetted partial regions of at least one reference region and a second maximum, which is caused by wetted partial regions. As a further example, U.S. Pat. No. 6,993,172 B2 discloses a method and system for employing pixel-based, signal-intensity data contained within areas of a scanned image of a molecular array corresponding to features and feature backgrounds in order to determine whether or not the features or feature backgrounds have non-uniform signal intensities and are thus outlier features and outlier feature backgrounds.

As an example, U.S. Publication No. 2015/308961 A1 describes color quantification of chemical test pads and titration of analytes which can be performed under different lighting conditions. In one embodiment, the lighting condition is estimated under which a digital image is captured and utilized to select a set of reference colors from which the quantified color is compared to determine the titration. In another embodiment, a plurality of comparisons are made with different lighting conditions with the result having the highest confidence level being selected to determine the titration.

DE 196 30 160 A1 discloses an analysis system for evaluating test elements having means for determining whether a sufficient quantity of sample liquid has been uniformly applied to the delivery zone of a test element. In a first embodiment the analysis system comprises at least two light sources which illuminate regions of the delivery zone or evaluation zone of the test element which are separate from one another or at least do not completely overlap. Further, the analysis system comprises a control unit with which the at least two light sources can be activated separately from one another, at least one sensor, which detects the light reflected from the evaluation zone or transmitted through the evaluation zone and supplies output signals corresponding to the light intensity, and an evaluation unit.

In U.S. Publication No. 2016/153912 A1, a method for detecting at least one analyte in at least one sample of a body fluid is disclosed. Therein, at least one test element is used, the at least one test element having at least one test field with at least one test chemistry is used, wherein the test chemistry is adapted to perform at least one optically detectable detection reaction in the presence of the analyte. The method comprises acquiring an image sequence of images of the test field by using at least one image detector. Each image comprises a plurality of pixels. The method further comprises detecting at least one characteristic feature of the test field in the images of the image sequence. The method further comprises correcting a relative position change between the image detector and the test field in the image sequence by using the characteristic feature, thereby obtaining a sequence of corrected images.

Despite the advantages involved in using consumer-electronics having a camera for the purpose of evaluating analytical measurements, several technical challenges remain. Specifically, measurements of faulty or non-ideal evaluation areas, so far, are generally discarded or limited to the occurrence of specific defects such as methods in which areas having insufficient sample are not used in analyte concentration determination known, e.g., from EP 1 359 409 A2. The common approach of discarding such measurements, generally may lead to significant inconvenience for users and/or patients.

SUMMARY

This disclosure teaches methods and devices which address the above-mentioned technical challenges of analytical measurements using mobile devices such as consumer-electronics mobile devices, specifically multipurpose mobile devices which are not dedicated to analytical measurements such as smart phones or tablet computers. Specifically, methods and devices are disclosed which are widely applicable to available mobile devices and which are suited to increase measurement accuracy and convenience for the user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "test strip," "camera," "sample," and "test field," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a method for performing an analytical measurement is disclosed. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed.

Generally, the method for performing an analytical measurement comprises the following steps:
  a) providing at least one mobile device having at least one camera;
  b) providing at least one test strip configured for performing a color-change detection reaction and applying at least one sample to the test strip, specifically to at least one test field of the test strip, the test field containing at least one test chemical for detecting at least one analyte in the sample;
  c) capturing at least one image of at least a part of the test strip by using the camera, wherein said image is comprised of a plurality of pixels;
  d) determining, specifically identifying, at least one region of interest in the image, and associating a first sub-set of pixels with the region of interest;
  e) evaluating a color distribution within the first sub-set of pixels and eliminating outliers in the first sub-set of pixels;
  f) determining, specifically identifying, at least one sub-region of interest within the region of interest, the sub-region of interest having a smaller area than the region of interest, and associating a second sub-set of pixels with the sub-region of interest; and
  g) comparing at least one mean value of the color distribution of the first sub-set of pixels and at least one mean value of a color distribution of the second sub-set of pixels and determining thereby at least one item of homogeneity information on a homogeneity of the image.

The term "analytical measurement" as used herein is a broad term and is to be given its ordinary and customary meaning to a person of ordinary skill in the art and is not to be limited to a special or customized meaning. The term specifically may refer, without limitation, to a quantitatively and/or qualitatively determination of at least one analyte in an arbitrary sample. For example, the sample may comprise a body fluid, such as blood, interstitial fluid, urine, saliva or other types of body fluids. The result of the analytical measurement, as an example, may be a concentration of the analyte and/or the presence or absence of the analyte to be determined. Specifically, as an example, the analytical measurement may be a blood glucose measurement, thus the result of the analytical measurement may for example be a blood glucose concentration.

The term "analyte" as used herein is a broad term and is to be given its ordinary and customary meaning to a person of ordinary skill in the art and is not to be limited to a special or customized meaning. The term specifically may refer, without limitation, to one or more specific chemical compounds and/or other parameters to be detected and/or measured. As an example, the at least one analyte may be a chemical compound which takes part in metabolism, such as one or more of glucose, cholesterol or triglycerides. Additionally or alternatively, other types of analytes or parameters may be determined, e.g., a pH value.

In step a) the mobile device having the at least one camera is provided. The term "mobile device" as used herein is a broad term and is to be given its ordinary and customary meaning to a person of ordinary skill in the art and is not to be limited to a special or customized meaning. The term specifically may refer, without limitation, to a mobile electronics device, more specifically to a mobile communication device such as a cell phone or smart phone. Additionally or alternatively, as will be outlined in further detail below, the mobile device may also refer to a tablet computer or another type of portable computer having at least one camera.

As further used herein, the term "camera" is a broad term and is to be given its ordinary and customary meaning to a person of ordinary skill in the art and is not to be limited to a special or customized meaning. The term specifically may refer, without limitation, to a device configured for recording spatially resolved optical data, such as one or more images. The camera specifically may comprise one or more camera chips or imaging devices, such as one or more CCD and/or CMOS chips. The camera generally may comprise a one-dimensional or two-dimensional array of image sensors, such as pixels. As an example, the camera may comprise at least 10 pixels in at least one dimension, such as at least 10 pixels in each dimension. It shall be noted, however, that other cameras are also feasible. This disclosure specifically shall be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible. The camera, besides at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually.

The camera specifically may be a color camera. Thus, such as for each pixel, color information may be provided or generated, such as color values for three colors R, G, B. A larger number of color values is also feasible, such as four colors for each pixel. Color cameras are generally known to the skilled person. Thus, as an example, each pixel of the camera chip may have three or more different color sensors, such as color recording pixels like one pixel for red (R), one pixel for yellow (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as C, M, Y, K. The color sensitivities of the pixels may be generated by color filters or by appropriate intrinsic sensitivities of the sensor elements used in the camera pixels. These techniques are generally known to the skilled person.

In step b) the at least one test strip is provided. The term "test strip" as used herein is a broad term and is to be given its ordinary and customary meaning to a person of ordinary skill in the art and is not to be limited to a special or customized meaning. The term specifically may refer, without limitation, to an arbitrary element or device configured for performing a color-change detection reaction. The test strip may particularly have a test field containing at least one test chemical for detecting the at least one analyte. The test element, as an example, may comprise at least one substrate, such as at least one carrier, with the at least one test field applied thereto or integrated therein. As an example, the at least one carrier may be strip-shaped, thereby rendering the test element a test strip. These test strips are generally widely in use and available. One test strip may carry a single test field or a plurality of test fields having identical or different test chemicals comprised therein.

As further used herein, the term "test field" is a broad term and is to be given its ordinary and customary meaning to a person of ordinary skill in the art and is not to be limited to a special or customized meaning. The term specifically may refer, without limitation, to a coherent amount of the test chemical, such as to a field, e.g., a field of round, polygonal or rectangular shape, having one or more layers of material, with at least one layer of the test field having the test chemical comprised therein. Other layers may be present providing specific optical properties such as reflective properties, providing spreading properties for spreading the sample or providing separation properties such as for separating of particulate components of the sample, such as cellular components.

The term "test chemical" as used herein is a broad term and is to be given its ordinary and customary meaning to a person of ordinary skill in the art and is not to be limited to a special or customized meaning. The term specifically may refer, without limitation, to a chemical compound or a plurality of chemical compounds such as a mixture of chemical compounds suited for performing a detection reaction in the presence of the analyte, wherein the detection reaction is detectable by specific means, such as optically. The detection reaction specifically may be analyte-specific. The test chemical, in the present case, specifically may be an optical test chemical, such as a color-change test chemical which changes in color in the presence of the analyte. The color change specifically may depend on the amount of analyte present in the sample. The test chemical, as an example, may comprise at least one enzyme, such as glucose oxidase and/or glucose dehydrogenase. Additionally, other components may be present, such as one or more dyes, mediators and the like. Test chemicals are generally known to the skilled person and reference may be made to J. Hones et al.: Diabetes Technology and Therapeutics, Vol. 10, Supplement 1, 2008, pp. 10-26. Other test chemicals, however, are feasible, too.

In step c) the at least one image is captured by using the camera. The term "image" as used herein is a broad term and is to be given its ordinary and customary meaning to a person of ordinary skill in the art and is not to be limited to a special or customized meaning. The term specifically may refer, without limitation, to data or information recorded by using the camera, such as a plurality of electronic readings from the imaging device, such as the pixels of the camera chip. Thus, as an example, the image may comprise a one-dimensional or two-dimensional array of data. The image itself, thus, may comprise pixels, the pixels of the image, as an example, correlating to pixels of the camera chip. Consequently, when referring to "pixels," reference is either made to the units of image information generated by the single pixels of the camera chip or to the single pixels of the camera chip directly.

In step d) the at least one region of interest is determined, specifically identified, within the image. The term "region of interest" as used herein is a broad term and is to be given its ordinary and customary meaning to a person of ordinary skill in the art and is not to be limited to a special or customized meaning. The term specifically may refer, without limitation, to a subset of data within a larger data set, the subset being identified for a particular purpose. As an example, the term may refer to at least one partial image or region within an image, determined for a certain purpose.

Further, the first sub-set of pixels is associated with the region of interest. As used herein, the term "sub-set of pixels" is a broad term and is to be given its ordinary and customary meaning to a person of ordinary skill in the art and is not to be limited to a special or customized meaning. The term specifically may refer, without limitation, to a partial quantity of picture elements, such as pixels, within an image or picture. In the present context, the sub-set of pixels may specifically be a quantity of pixels within the image involved in displaying the region of interest within the image.

In step e) the color distribution within the first sub-set of pixels is evaluated. As used herein, the term "color distribution" is a broad term and is to be given its ordinary and customary meaning to a person of ordinary skill in the art and is not to be limited to a special or customized meaning. The term specifically may refer, without limitation, to a dispersion of color in a defined set of data, such as in an image. The color distribution may specifically be represented in a histogram, e.g., an image histogram, derived by counting the number of pixels of each of a given set of color ranges in a color coordinate system. As used herein, the term "color coordinate system" is a broad term and is to be given its ordinary and customary meaning to a person of ordinary skill in the art and is not to be limited to a special or customized meaning. The term specifically may refer, without limitation, to an arbitrary coordinate system by which a color of an object, such as a color of a test field or a color of an image recorded by a camera, may be characterized, such as mathematically or physically. Various color coordinate systems are generally known to the skilled person, such as color coordinate systems defined by CIE. The color coordinates, in their entirety, may span or define a color space, such as by defining three or four basis vectors.

Further, outliers in the first sub-set of pixels are eliminated. The term "outliers" as used herein is a broad term and is to be given its ordinary and customary meaning to a person of ordinary skill in the art and is not to be limited to a special or customized meaning. The term specifically may refer, without limitation, to a statistical exceptional data point or value. Specifically, an outlier may be a value in a set of data that does not fit a statistical pattern describing most other data points within the set of data. Thus, as an example, a percentile method may be used for determining which data points are regular and which data points are outliers, such as by determining percentile thresholds. Additionally or alternatively, other means may be used for defining regular data points and outliers, such as simple threshold procedures.

For example, regular data points may be equal to or above a lower percentile threshold and/or equal to or below an upper percentile threshold. Thus, outliers may be data points below the lower percentile threshold and/or above the upper percentile threshold. In particular, the lower percentile threshold may for example range from $>0^{th}$ percentile to the $35^{th}$ percentile, wherein the $0^{th}$ percentile indicates that no data point exists below this percentile threshold, preferably from the $5^{th}$ percentile to the $30^{th}$ percentile, more preferably from the $15^{th}$ to the $25^{th}$ percentile, even more preferably the lower percentile threshold may particularly be the $25^{th}$ percentile Further, particular additionally and/or in combination with the lower percentile threshold, outliers may particularly be data points above the upper percentile threshold. In particular, the upper percentile threshold may for example range from the $65^{th}$ percentile to $<100^{th}$ percentile, wherein the $100^{th}$ percentile indicates that all data points fall at or below this percentile threshold, preferably from the $70^{th}$ percentile to the $95^{th}$ percentile, more preferably from the $75^{th}$ percentile to the $85^{th}$ percentile, even more preferably the upper percentile threshold may particularly be the $75^{th}$ percentile. Specifically, as indicated above, for determining which data points are regular and which data points are outliers, any combination of the above defined lower percentile thresholds and the above defined upper percentile thresholds may be used.

Step f) comprises determining, specifically identifying, the at least one sub-region of interest within the region of interest, the sub-region of interest having a smaller area than the region of interest. Specifically, a second sub-set of pixels is associated with the sub-region of interest.

In step g) the at least one mean value of the color distribution of the first sub-set of pixels and the at least one mean value of the color distribution of the second sub-set of pixels is compared. Thereby, the at least one item of homogeneity information on the homogeneity of the image is determined. The term "mean value" as used herein is a broad term and is to be given its ordinary and customary meaning to a person of ordinary skill in the art and is not to be limited to a special or customized meaning. The term specifically may refer, without limitation, to a value or number being representative for all the values in a set of data, such as to a value or number calculated by using all the values in a set of data, the value representing, e.g., an approximate middle of the entire values in the set of data. Specifically, the mean value may be selected from the group consisting of an arithmetic mean value, a geometric mean value or a median. Specifically, the mean value may be calculated by using the sum of values of a discrete set of data divided by the number of values of the discrete set of data. As an example, the mean value of the color distribution, in the present case, may specifically be calculated by summing up the colors of the pixels within a set of pixels and dividing the result by the number of pixels within the set of pixels. Other calculation methods are possible, such as for example individually weighing or rating all or part of the pixels.

The term "item of homogeneity information" (used herein interchangeably with the term "homogeneity information") as used herein is a broad term and is to be given its ordinary and customary meaning to a person of ordinary skill in the art and is not to be limited to a special or customized meaning. The term specifically may refer, without limitation, to an indication, quantification or information regarding the homogeneity of an arbitrary system. Specifically in the present case, the term may refer to an indication or information regarding the homogeneity of the image captured by using the camera of the mobile device. The item of homogeneity information, as an example, may be Boolean or digital information, such as indicating one or more of "homogeneous" or "inhomogeneous," "suited" or "not suited"/"unsuited." Thus, as an example, in case the mean value of the color distribution of the first sub-set of pixels may be compared with the mean value of the color distribution of the second sub-set of pixels and found to differ from each other by a value greater than a maximum tolerance acceptable in an analytical measurement, the image may be unsuited for performing the analytical measurement. For example, in case the mean values of the color distributions of the first and second sub-sets of pixels differ by more than a maximum tolerance acceptable in blood glucose measurement, the image may be found to be unsuited for performing the blood glucose measurement, thus the item of homogeneity information may indicate the image being "not suited." Alternatively, however, as already outlined above, the homogeneity may also be quantified.

The term "homogeneity" as used herein is a broad term and is to be given its ordinary and customary meaning to a person of ordinary skill in the art and is not to be limited to a special or customized meaning. The term specifically may refer, without limitation, to a uniformity of characteristics or properties, such as for example an alikeness of colors, specifically an alikeness of colors of pixels. The homogeneity, as an example, may be quantified by indicating a broadness of a distribution of values. For example, the homogeneity may be indicated in terms of a distance between colors within a color coordinate system.

The method according to the first aspect of this disclosure may further be refined by comprising the following steps:
- h) if the at least one item of homogeneity information indicates the image being unsuited for performing the analytical measurement, aborting the method for performing the analytical measurement; and
- i) if the at least one item of homogeneity information indicates the image being suited for performing the analytical measurement, evaluating the image and deriving at least one analytical information, specifically at least one item of information on a concentration of at least one analyte in the sample.

The method may make use of the at least one item of homogeneity information which, as an example, may be or may comprise digital information or Boolean information such as indicated above, e.g., "suited" or "not suited" for performing the analytical measurement. Depending on this homogeneity information, the method may branch in between steps h) and i), wherein the inquiry regarding the homogeneity may be programmed, e.g., as an "if . . . " routine, an "if . . . else . . . " routine or the like.

The term "item of information on a concentration of at least one analyte" as used herein is a broad term and is to be given its ordinary and customary meaning to a person of ordinary skill in the art and is not to be limited to a special or customized meaning. The term specifically may refer, without limitation, to an indication or information regarding a concentration of at least one analyte within an arbitrary sample As an example, the item of information on the concentration of the at least one analyte in the sample may specifically be a blood glucose concentration in a blood sample.

Further, the method step g) may comprise comparing an absolute value of a difference between the mean value of the color distribution of the first sub-set of pixels and the mean value of the color distribution of the second sub-set of pixels with at least one threshold value. The term "difference" as used herein is a broad term and is to be given its ordinary and customary meaning to a person of ordinary skill in the art and is not to be limited to a special or customized meaning. The term specifically may refer, without limitation, to an absolute variance or gap between at least two values or numbers. Specifically, the difference between values of color distribution, such as for example the difference between the mean value of the color distribution of the first sub-set of pixels and the mean value of the color distribution of the second sub-set of pixels may indicate a distance between the values of color distribution within the color coordinate system. The distance, for example, may be given and/or indicated in "counts," such as in a quantity of steps within the histogram, specifically the distance may be indicated by an absolute number of counts having a predefined step size within the color coordinate system.

The term "comparing," without limitation, may refer to a process of simply determining if a first value is smaller, greater or equal to a second value or the like. Additionally or alternatively, a difference between the values may also be quantified. Other means on comparison may also be used, thereby generally generating information on a relationship between the values to be compared.

The term "threshold" as used herein is a broad term and is to be given its ordinary and customary meaning to a person of ordinary skill in the art and is not to be limited to a special or customized meaning. The term specifically may refer, without limitation, to an arbitrary value indicating a boundary and/or border within a system. The threshold may for example indicate a value and/or a level below which something may be true and above which it may not be true. Specifically, within this disclosure, the threshold value may be a value below which the image may be suited for performing the analytical measurement, and above which the image may not be suited. Particularly, the threshold value may for example be used when determining the item of homogeneity information. For example, the at least one item of homogeneity information may indicate the image being suited for performing the analytical measurement in case the absolute value of the difference, specifically the difference between the mean value of the color distribution of the first sub set of pixels and the mean value of the color distribution of the second sub set of pixels, is smaller than the threshold value or if the absolute value of the difference does not exceed the threshold value.

Specifically, the method may comprise defining a minimum accuracy of the analytical measurement. In particular, the method may further comprise determining the threshold by transforming the minimum accuracy of the analytical measurement into the threshold value by using a determinable relationship between the color distribution and the analyte measurement, specifically between a mean value of the color distribution of the region of interest and the analyte concentration in the sample.

Further, the method step e) may comprise evaluating the color distribution for at least two color coordinates. More preferably, the method step e) may comprise evaluating the color distribution for at least three color coordinates. Particularly, the color distribution may be evaluated independently, such as for example in an independent manner from each other, for the at least two color coordinates, more preferably for the at least three color coordinates. As an example, the color distribution may be evaluated for a first color coordinate, e.g., indicating values for the color red, and a second color coordinate, e.g., indicating values for the color yellow, and a third color coordinate, e.g., indicating values for the color blue, in a timely sequential fashion.

Specifically, method step g) may be performed independently for all of the at least two color coordinates. For example, the mean value of the color distribution of the first sub-set of pixels and the mean value of the color distribution of the second sub-set of pixels may be compared for all of the at least two color coordinates independently, particularly in an independent manner. As an example, the mean values of the color distribution may be compared in a timely sequential fashion for all of the at least two color coordinates.

Particularly, the at least one item of homogeneity information may be determined for each of the at least two color coordinates. Specifically, the homogeneity of the image may be evaluated for each color coordinate separately. Particularly, in case the item of homogeneity information determined for a first color coordinate indicates the image not being suited for performing the analytical measurement, the image in general may be indicated as not being suited for performing the analytical measurement.

As an example, the absolute value of the difference between the mean value of the color distribution of the first subset of pixels and the mean value of the color distributions of the second subset of pixels may be compared independently with the at least one threshold value for each of the at least two color coordinates.

Further, the test strip may comprise at least one test field and at least one reference color field. Specifically, the method step c) may be performed such that the at least one image contains at least one image or at least one partial image of the test field and at least one image or at least one partial image of the reference color field. In particular, method steps d) to g) may be performed both for the image or partial image of the test field and for the image or partial image of the reference color field, specifically independently.

As an example, the reference color field may contain at least one white field. Specifically, the reference color field may comprise at least one field having a white color, particularly a predetermined white color or shade of white color. For example, the reference color field may particularly contain a color of the test strip, such as a color of the substrate or test strip carrier. Thus, as an example, the reference color field may simply be the substrate, e.g., the test strip carrier, itself.

Specifically, the region of interest and the sub-region of interest may each have a shape which is, independently, selected from the group consisting of: a rectangular shape; a square shape; a round shape; a circular shape; and a subtraction and/or combination thereof.

Further, the method step e) may comprise eliminating pixels having a color, specifically color coordinates, outside an acceptance interval. Particularly, pixels having a color outside an acceptance interval of $[p_1-\Delta p_1, p_2+\Delta p_2]$, with $p_1$ being a lower percentile, $p_2$ being an upper percentile and $\Delta p_1$, $\Delta p_2$ being positive tolerance ranges, may be eliminated.

In particular, $p_1$ may be the 25% quantile of the color distribution and $p_2$ may be the 75% quantile of the color distribution. Specifically, the 25% quantile may also be referred to as "lower quartile" and similarly the 75% quantile may also be referred to as "upper quartile."

As an example, $\Delta p_1$ and $\Delta p_2$ may be described by using the following equations, further referred to as equation (1) and equation (2):

$$\Delta p_1 = f_1 \cdot (p_2 - p_1) \quad (1)$$

$$\text{and } \Delta p_2 = f_2 \cdot (p_2 - p_1) \quad (2)$$

with $f_1$, $f_2$ being positive tolerance factors, specifically with $f_1, f_2 \geq 1$, more specifically with $1.0 \leq f_1, f_2 < 2.0$, more specifically with $1.3 \leq f_1, f_2 \leq 1.7$, more specifically with $f_1, f_2 = 1.5$.

Particularly, the acceptance interval may be $[p_1-1.5 \cdot L, p_2+1.5 \cdot L]$, with L being the range from quantile $p_1$ to quantile $p_2$. Specifically, in the particular case of $p_1$ being the 25% quantile and $p_2$ being the 75% quantile, the range L may be the interquartile range (IQR), thus for example L=IQR.

Further, method step d) may comprise determining the region of interest by using a pattern recognition method for identifying in the image at least one item selected from the group consisting of: the test field; a part of the test field; a reference color field; a part of a reference color field.

Specifically, a center of the region of interest may be located at a center of the test field or at a center of the reference color field within the image. The term "center" as used herein is a broad term and is to be given its ordinary and customary meaning to a person of ordinary skill in the art and is not to be limited to a special or customized meaning. The term specifically may refer, without limitation, to a point or location indicating a middle of a form or object. Specifically, the center may be a point within a circle or sphere equally distant from all points of the circumference or surface, or a point within a regular polygon equally distant from all vertices.

As an example, the at least one edge of the test field or the reference color field, preferably all edges of the test field or the reference color field, may be excluded from the region of interest. Particularly, edges and vertices of the test field or the reference color field may not be comprised within the region of interest.

Particularly, the center of the sub-region of interest may be located at the center of the region of interest.

Further, the method may comprise comparing the number of pixels within the first sub-set of pixels with at least one threshold value, thereby determining at least one item of size sufficiency information on a sufficiency of a size of the region of interest. Additionally, the method may comprise aborting the method for performing the analytical measurement, in case the at least one item of size sufficiency information indicates the region of interest being of a non-sufficient size. Particularly, if the at least one item of size sufficiency information indicates the region of interest being of a non-sufficient size, the method for performing the analytical measurement may be aborted.

As an example, the threshold value may be selected from a group consisting of: an absolute threshold value; a relative threshold value; specifically a relative threshold value depending on the number of pixels in the first sub-set of pixels.

Further, the method may comprise comparing the number of pixels in the first sub-set of pixels before eliminating the outliers in method step e) with the number of pixels in the first sub-set of pixels after eliminating the outliers in step e).

In particular, if the number of pixels in the first subset of pixels after eliminating the outliers in step e) is smaller than a predetermined percentage of the number of pixels in the first sub-set of pixels before eliminating the outliers in step e), the method for performing the analytical measurement may be aborted.

In a further aspect of this disclosure, a computer program including computer-executable instructions for performing the method according to any one of the embodiments as described herein is disclosed. Specifically the computer-executable instructions may be suited for performing method steps d), e), f) and g) and optionally one or more of the steps h) and i). In particular, the program is executed on a computer or a computer network, specifically on a processor of a mobile device having at least one camera.

Thus, generally speaking, disclosed and proposed herein is a computer program including computer-executable instructions for performing the method according to this disclosure in one or more of the embodiments enclosed herein when the program is executed on a computer or computer network. Specifically, the computer program may be stored on a computer-readable data carrier. Thus, specifically, one, more than one or even all of method steps as indicated above may be performed by using a computer or a computer network, preferably by using a computer program. The computer specifically may be fully or partially integrated into the mobile device, and the computer programs specifically may be embodied as a software app. Alternatively, however, at least part of the computer may also be located outside the mobile device.

Further disclosed and proposed herein is a data carrier having a data structure stored thereon, which, after loading into a computer or computer network, such as into a working memory or main memory of the computer or computer network, may execute the method according to one or more of the embodiments disclosed herein, specifically one or more of the method steps mentioned above.

Further disclosed and proposed herein is a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, disclosed and proposed herein is a modulated data signal which contains instructions readable by a computer system or computer network, for performing the method according to one or more of the embodiments disclosed herein, specifically one or more of the method steps mentioned above.

Specifically, further disclosed herein are:
a computer or computer network comprising at least one processor, wherein the processor is adapted to perform the method according to one of the embodiments described in this description,
a computer loadable data structure that is adapted to perform the method according to one of the embodiments described in this description while the data structure is being executed on a computer,
a computer program, wherein the computer program is adapted to perform the method according to one of the embodiments described in this description while the program is being executed on a computer,
a computer program comprising program means for performing the method according to one of the embodiments described in this description while the computer program is being executed on a computer or on a computer network,
a computer program comprising program means according to the preceding embodiment, wherein the program means are stored on a storage medium readable to a computer,
a storage medium, wherein a data structure is stored on the storage medium and wherein the data structure is adapted to perform the method according to one of the embodiments described in this description after having been loaded into a main and/or working storage of a computer or of a computer network, and
a computer program product having program code means, wherein the program code means can be stored or are stored on a storage medium, for performing the method according to one of the embodiments described in this description, if the program code means are executed on a computer or on a computer network.

In a further aspect of this disclosure, a mobile device for performing an analytical measurement is disclosed. The mobile device having at least one camera. The mobile device being configured for performing the at least one analytical measurement by using the following steps:
A) capturing at least one image of at least a part of a test strip by using the camera, wherein said image is comprised of a plurality of pixels;
B) determining, specifically identifying, at least one region of interest in the image, and associating a first sub-set of pixels with the region of interest;
C) evaluating a color distribution within the first sub-set of pixels and eliminating outliers in the first sub-set of pixels;
D) determining, specifically identifying, at least one sub-region of interest within the region of interest, the sub-region of interest having a smaller area than the region of interest, and associating a second sub-set of pixels with the sub-region of interest; and
E) comparing at least one mean value of the color distribution of the first sub-set of pixels and at least one mean value of a color distribution of the second sub-set of pixels and determining thereby at least one item of homogeneity information on a homogeneity of the image.

For most of the terms used herein and possible definitions, reference may be made to the description of the methods above.

The mobile device may comprise at least one processor. Specifically, the processor may be programmed to perform steps B)-E).

For possible definitions or embodiments, reference may be made to the description of the method as given above. Thus, particularly, the mobile device, specifically by using the processor, may be configured for performing the method for performing an analytical measurement according to any one of the embodiments described above or described in further detail below.

In a further aspect of this disclosure, a kit for performing an analytical measurement is disclosed. The kit comprises:
at least one mobile device; and
at least one test strip configured for performing a color-change detection reaction, specifically an optical test strip, specifically a test strip having at least one test field, the test field containing at least one test chemical for detecting at least one analyte in the sample.

Again, for possible definitions of terms and possible embodiments, reference may be made to the description given above or described in further detail below.

The methods and devices according to this disclosure may provide a large number of advantages over known methods and devices for analytical measurements. Thus, specifically, a process of performing an analytical measurement as suggested in this disclosure may be less time-consuming, compared to other processes known in the art. In particular, this disclosure may allow a usage of slightly defective images or images containing faulty or non-ideal evaluation areas, such as, for example, the test field or the reference color field, for performing the analytical measurement. This disclosure may allow a usage of images that otherwise would have been discarded, thus providing means for a less time-consuming and more practical performance of an analytical measurement, than known methods and devices.

Further, this disclosure may improve a reliability and a user-friendliness of the process of performing an analytical measurement, compared to processes known from the art. Specifically, this disclosure may improve the reliability and user-friendliness of an application, e.g., an app, including computer-executable instructions for performing an analytical measurement, compared to known apps or computer programs. In particular, this disclosure may allow actively improving defective images or images containing faulty or non-ideal evaluation areas, thus allowing a usage of such images. As an example, by actively improving the image captured for performing an analytical measurement, this disclosure may increase a reliability and a usability of the process of performing the analytical measurement.

Summarizing and without excluding further possible embodiments, the following embodiments may be envisaged:

Embodiment 1

A method for performing an analytical measurement, comprising the following steps:
a) providing at least one mobile device having at least one camera;
b) providing at least one test strip configured for performing a color-change detection reaction and applying at least one sample to the test strip, specifically to at least one test field of the test strip, the test field containing at least one test chemical for detecting at least one analyte in the sample;
c) capturing at least one image of at least a part of the test strip by using the camera, wherein said image is comprised of a plurality of pixels;
d) determining, specifically identifying, at least one region of interest in the image, and associating a first sub-set of pixels with the region of interest;
e) evaluating a color distribution within the first sub-set of pixels and eliminating outliers in the first sub-set of pixels;
f) determining, specifically identifying, at least one sub-region of interest within the region of interest, the sub-region of interest having a smaller area than the region of interest, and associating a second sub-set of pixels with the sub-region of interest; and
g) comparing at least one mean value of the color distribution of the first sub-set of pixels and at least one mean value of a color distribution of the second sub-set of pixels and determining thereby at least one item of homogeneity information on a homogeneity of the image.

Embodiment 2

The method according to the preceding embodiment, the method further comprising:
h) if the at least one item of homogeneity information indicates the image being unsuited for performing the analytical measurement, aborting the method for performing the analytical measurement; and
i) if the at least one item of homogeneity information indicates the image being suited for performing the analytical measurement, evaluating the image and deriving at least one analytical information, specifically at least one item of information on a concentration of at least one analyte in the sample.

Embodiment 3

The method according to any one of the preceding embodiments, wherein the method step g) comprises comparing an absolute value of a difference between the mean value of the color distribution of the first sub-set of pixels and the mean value of the color distribution of the second sub-set of pixels with at least one threshold value.

Embodiment 4

The method according to the preceding embodiment, wherein the at least one item of homogeneity information indicates the image being suited for performing the analytical measurement in case the absolute value of the difference is smaller than the threshold value or if the absolute value of the difference does not exceed the threshold value.

Embodiment 5

The method according to any one of the two preceding embodiments, wherein the method comprises defining a minimum accuracy of the analytical measurement, wherein the method further comprises determining the threshold by transforming the minimum accuracy of the analytical measurement into the threshold value by using a determinable relationship between the color distribution and the analyte measurement, specifically between a mean value of the color distribution of the region of interest and the analyte concentration in the sample.

Embodiment 6

The method according to any one of the preceding embodiments, wherein step e) comprises evaluating the color distribution for at least two color coordinates, more preferably for at least three color coordinates, specifically independently.

Embodiment 7

The method according to the preceding embodiment, wherein, step g) is performed independently for all of the at least two color coordinates.

Embodiment 8

The method according to the preceding embodiment, wherein at least one item of homogeneity information is determined for each of the at least two color coordinates.

Embodiment 9

The method according to any one of the preceding embodiments, wherein the test strip comprises at least one test field and at least one reference color field, wherein step c) is performed such that the at least one image contains at least one image or at least one partial image of the test field and at least one image or at least one partial image of the reference color field, wherein steps d) to g) are performed both for the image or partial image of the test field and for the image or partial image of the reference color field, specifically independently.

Embodiment 10

The method according to the preceding embodiment, wherein the reference color field contains at least one white field.

Embodiment 11

The method according to any one of the preceding embodiments, wherein the region of interest and the subregion of interest each have a shape which is, independently, selected from the group consisting of: a rectangular shape; a square shape; a round shape; a circular shape; and a subtraction and/or combination thereof.

Embodiment 12

The method according to any one of the preceding embodiments, wherein step e) is performed such that the eliminating of outliers in the first sub-set of pixels is performed by using one or both of a histogram analysis or a percentile analysis of the color distribution.

Embodiment 13

The method according to any one of the preceding embodiments, wherein step e) comprises eliminating pixels having a color, specifically color coordinates, outside an acceptance interval of $[p_1-\Delta p_1, p_2+\Delta p_2]$, with $p_1$ being a lower percentile, $p_2$ being an upper percentile and $\Delta p_1$, $\Delta p_2$ being positive tolerance ranges.

Embodiment 14

The method according to the preceding embodiment, wherein $p_1$ is the 25% quantile of the color distribution and wherein $p_2$ is the 75% quantile of the color distribution.

Embodiment 15

The method according to any one of the two preceding embodiments, wherein $\Delta p_1 = f_1 \cdot (p_2 - p_1)$, and $\Delta p_2 = f_2 \cdot (p_2 - p_1)$, with $f_1$, $f_2$ being positive tolerance factors, specifically with $f_1, f_2 \geq 1$, more specifically with $1.0 \leq f_1, f_2 \leq 2.0$, more specifically with $1.3 \leq f_1, f_2 \leq 1.7$, more specifically with $f_1, f_2 = 1.5$.

Embodiment 16

The method according to the preceding embodiment, wherein $p_1$ is the 25% quantile of the color distribution and wherein $p_2$ is the 75% quantile of the color distribution, wherein the acceptance interval is $[p_1-1.5\cdot L, p_2+1.5\cdot L]$, with L being the range from quantile $p_1$ to quantile $p_2$.

Embodiment 17

The method according to any one of the preceding embodiments, wherein step d) comprises determining the region of interest by using a pattern recognition method for identifying in the image at least one item selected from the group consisting of: the test field; a part of the test field; a reference color field; a part of a reference color field.

Embodiment 18

The method according to the preceding embodiment, wherein a center of the region of interest is located at a center of the test field or at a center of the reference color field within the image.

Embodiment 19

The method according to any one of the two preceding embodiments, wherein at least one edge of the test field or the reference color field, preferably all edges of the test field or the reference color field, is excluded from the region of interest.

Embodiment 20

The method according to any one of the two preceding embodiments, wherein a center of the sub-region of interest is located at the center of the region of interest.

Embodiment 21

The method according to any one of the preceding embodiments, wherein the method further comprises comparing the number of pixels within the first sub-set of pixels with at least one threshold value, thereby determining at least one item of size sufficiency information on a sufficiency of a size of the region of interest, wherein if the at least one item of size sufficiency information indicates the region of interest being of a non-sufficient size, aborting the method for performing the analytical measurement.

Embodiment 22

The method according to the preceding embodiment, wherein the threshold value is selected from a group consisting of: an absolute threshold value; a relative threshold value; specifically a relative threshold value depending on the number of pixels in the first sub-set of pixels.

Embodiment 23

The method according to any one of the preceding embodiments, wherein the method further comprises comparing the number of pixels in the first sub-set of pixels before eliminating the outliers in step e) with the number of pixels in the first sub-set of pixels after eliminating the outliers in step e).

Embodiment 24

The method according to the preceding embodiment, wherein, if the number of pixels in the first sub-set of pixels after eliminating the outliers in step e) is smaller than a predetermined percentage of the number of pixels in the first sub-set of pixels before eliminating the outliers in step e), the method for performing the analytical measurement is aborted.

Embodiment 25

A computer program including computer-executable instructions for performing the method according to any one of the preceding embodiments, specifically method steps d), e), f) and g) and optionally one or more of the steps h) and i), wherein the program is executed on a computer or a computer network, specifically on a processor of a mobile device having at least one camera.

Embodiment 26

A mobile device for performing an analytical measurement the mobile device having at least one camera, the mobile device being configured for performing the at least one analytical measurement by using the following steps:

A) capturing at least one image of at least a part of a test strip by using the camera, wherein said image is comprised of a plurality of pixels;
B) determining, specifically identifying, at least one region of interest in the image, and associating a first sub-set of pixels with the region of interest;
C) evaluating a color distribution within the first sub-set of pixels and eliminating outliers in the first sub-set of pixels;
D) determining, specifically identifying, at least one sub-region of interest within the region of interest, the sub-region of interest having a smaller area than the region of interest, and associating a second sub-set of pixels with the sub-region of interest; and
E) comparing at least one mean value of the color distribution of the first sub-set of pixels and at least one mean value of a color distribution of the second sub-set of pixels and determining thereby at least one item of homogeneity information on a homogeneity of the image.

Embodiment 27

The mobile device according to the preceding embodiment, wherein the mobile device comprises at least one processor, wherein the processor is programmed to perform steps B)-E).

Embodiment 28

The mobile device according to any one of the preceding embodiments referring to a mobile device, wherein the mobile device, specifically by using the processor, is configured for performing the method according to any one of the preceding method embodiments.

Embodiment 29

A kit for performing an analytical measurement, the kit comprising:
  at least one mobile device according to any one of the preceding embodiments referring to a mobile device; and
  at least one test strip configured for performing a color-change detection reaction, specifically an optical test strip, specifically a test strip having at least one test field, the test field containing at least one test chemical for detecting at least one analyte in the sample.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:
FIGS. 1 and 2 show flow charts of a method for performing an analytical measurement.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 3:
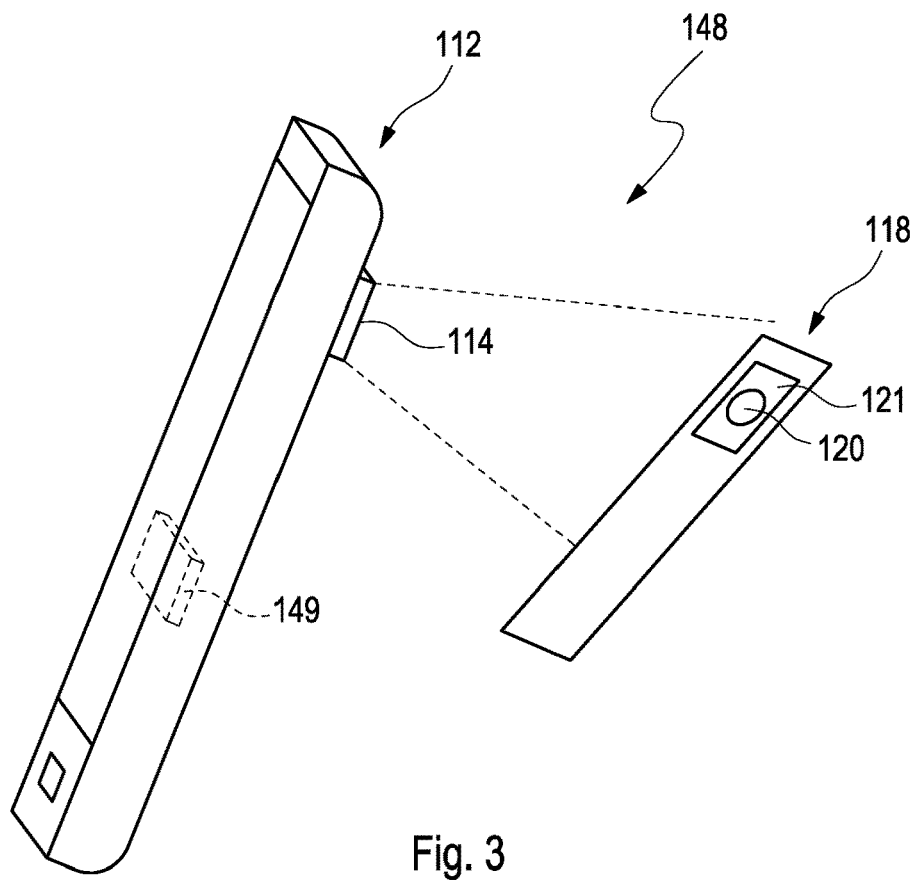
FIG. 3 shows a perspective view of an embodiment of a kit and a mobile device for performing an analytical measurement.

In FIG. 1, a flow chart of an embodiment of a method for performing an analytical measurement is shown. The method comprises step a) (method step 110) providing at least one mobile device 112 having at least one camera 114. As an example, the mobile device 112 having the at least one camera 114, as illustrated in FIG. 3, may be provided. The method further comprises step b) (method step 116) providing at least one test strip 118 configured for performing a color-change detection reaction and applying at least one sample to the test strip 118. The sample may specifically be applied to at least one test field 120 containing at least one test chemical for detecting at least one analyte in the sample. Specifically, the test strip 118 and the test field 120, as illustrated in FIG. 3, may be provided. Additionally, the test strip 118 may further comprise a reference color field 121.

The method further comprises step c) (method step 122) capturing at least one image 124 of at least a part of the test strip 118 by using the camera 114. Specifically, the image 124, as for example illustrated in FIG. 4, may be captured. The image 124 is comprised of a plurality of pixels. Further, the method comprises step d) (method step 126) determining, specifically identifying, at least one region of interest 128 in the image 124, and associating a first sub-set of pixels with the region of interest 128. Specifically, the region of interest 128, as for example illustrated in FIG. 5A, may be determined.

The method further comprises step e) (method step 130) evaluating a color distribution within the first sub-set of pixels and eliminating outliers in the first sub-set of pixels. Further, the method comprises step f) (method step 132) determining, specifically identifying, at least one sub-region of interest 134 within the region of interest 128, the sub-region of interest 134 having a smaller area than the region of interest 128, and associating a second sub-set of pixels with the sub-region of interest 134. The method further comprises step g) (method step 136) comparing at least one mean value of the color distribution of the first sub-set of pixels and at least one mean value of a color distribution of the second sub-set of pixels and determining thereby at least one item of homogeneity information on a homogeneity of the image 124.

As illustrated in FIG. 2, an embodiment of a method for performing an analytical measurement may additionally comprise a branching point 138. The branching point 138 may indicate a condition query, such as deciding between a first branch 140 and a second branch 142. For example, the condition query may make use of the item of homogeneity information. The item of homogeneity information may comprise Boolean information on the homogeneity of the image 124, such as "suited" ("y") or "not suited" ("n"). The first branch 140 indicates the image 124 being unsuited for performing the analytical measurement, thus the first branch 140 may lead to a step h) (method step 144) if the at least one item of homogeneity information indicates the image 124 being unsuited for performing the analytical measurement, aborting the method for performing the analytical measurement. Specifically, the blood glucose measurement may not be performed if the item of homogeneity information indicates the image 124 being "unsuited" for performing the blood glucose measurement.

The second branch 142 indicates the image 124 being suited for performing the analytical measurement. Thus, the second bronze may lead to a step i) (method step 146) if the at least one item of homogeneity information indicates the image 124 being suited for performing the analytical measurement, evaluating the image 124 and deriving at least one analytical information, specifically at least one item of information on a concentration of at least one analyte in the sample. Specifically, the blood glucose measurement may be performed if the item of homogeneity information indicates the image 124 being suited for performing the blood glucose measurement. Specifically, the at least one item of information on a concentration of the at least one analyte in the sample may be derived from the image 124.

In FIG. 3, an embodiment of a kit 148 and a mobile device for performing an analytical measurement is illustrated in a perspective view. The kit 148 comprises the at least one mobile device 112 and the at least one test strip 118 configured for performing a color-change detection reaction. The mobile device 112, having a camera 114, may further comprise a processor 149. The mobile device 112, specifically by using the processor 149, may be configured for performing the method illustrated in FIGS. 1 and 2. The test strip 118 may specifically be an optical test strip. In particular, as described above, the test strip 118 may specifically have at least one test field 120, the test field 120 containing at least one test chemical for detecting at least one analyte in the sample.

Figure 4:
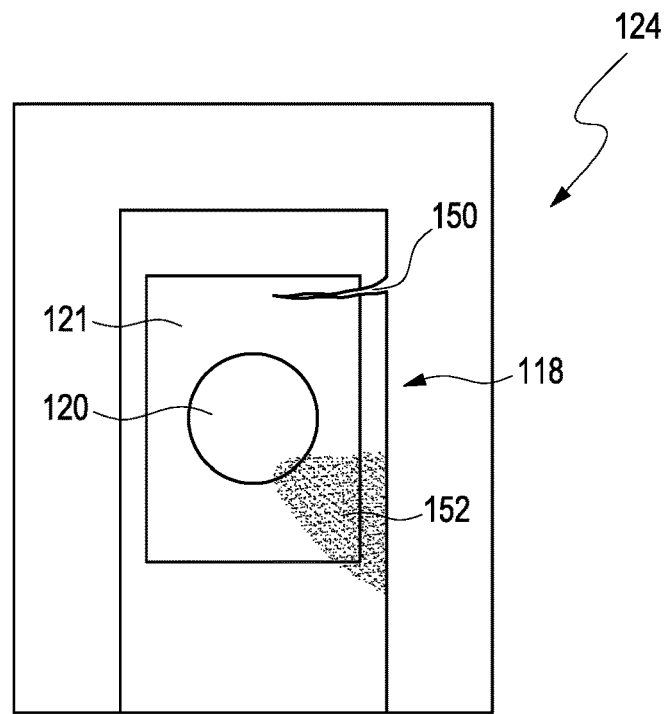
FIG. 4 shows an embodiment of an image captured by a mobile device.

The mobile device 112, as illustrated in FIG. 3, may capture the at least one image 124 of at least a part of the test strip 118, by using the camera 114. An embodiment of an image 124 captured by the mobile device 112 is shown in FIG. 4. Specifically, the image 124 is comprised of a plurality of pixels. As illustrated in FIG. 4, the image 124 of the at least part of the test strip 118 may show various faulty or non-ideal evaluation areas, such as for example damages 150 to the test strip 118 and/or contaminated or dirty areas 152 within the test field 120 or the reference color field 121.

Figure 5:
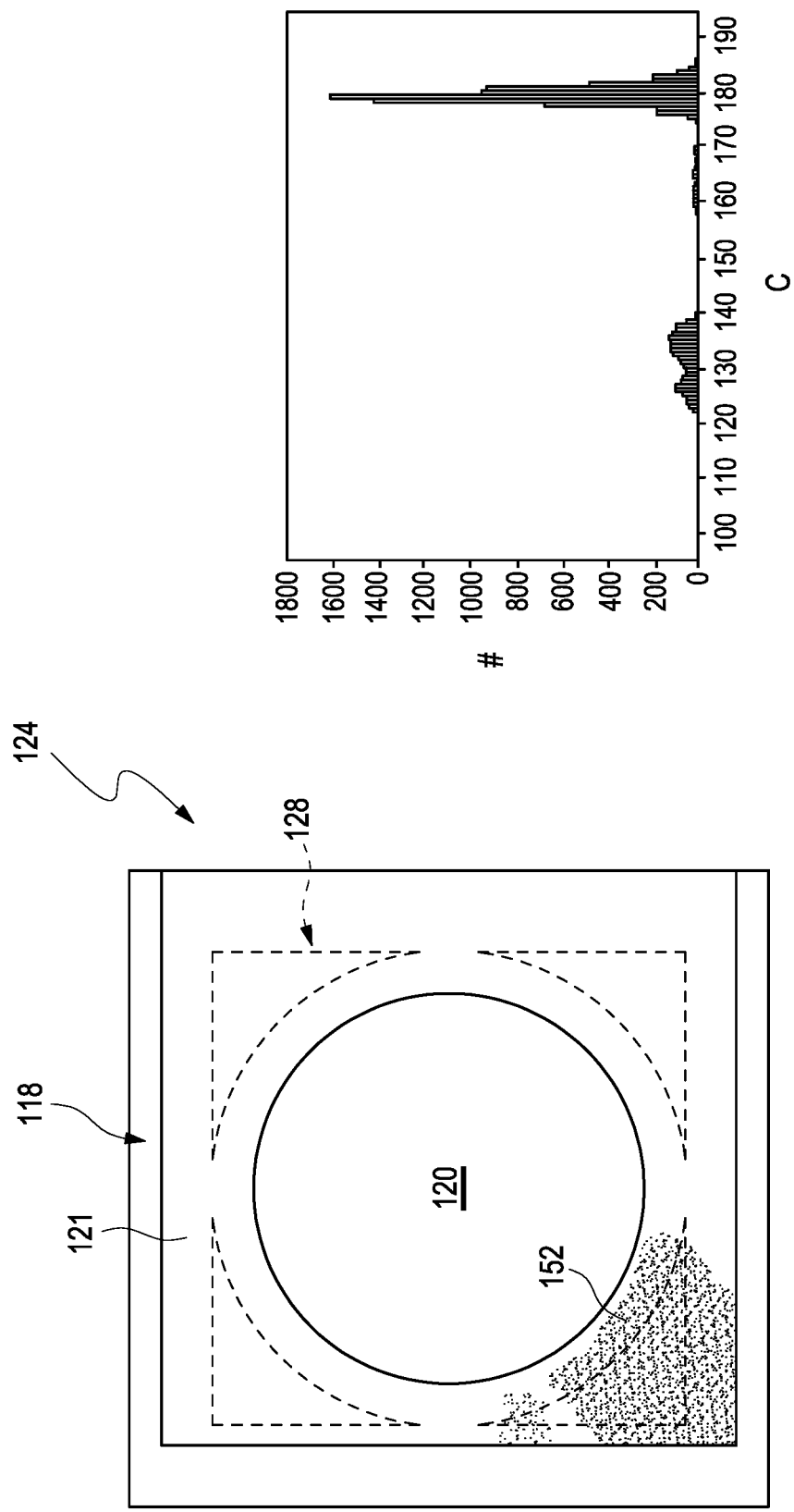
FIGS. 5A and 6A illustrate embodiments of images captured by a mobile device and a determined region of interest.
FIGS. 5B and 6B illustrate embodiments of histograms corresponding to FIGS. 5A and 6A.

Further, the at least one region of interest 128 may be determined within the image 124 and a first sub-set of pixels may be associated with the region of interest 128, as shown in FIG. 5A. The region of interest 128 may have a shape of a subtraction of a circular shape from a rectangular shape, e.g., illustrated by the dashed lines. As an example, contaminated or dirty areas 152 within the reference color field 121 may lie within the region of interest 128. The contaminated or dirty area 152 illustrated in FIG. 5A, may particularly be a red colored bloodstain. A histogram corresponding to the region of interest 128 illustrated in FIG. 5A, is shown in FIG. 5B. The histogram may be based on one color coordinate, such as for example the color coordinates indicating values for the color red. Specifically, the histogram may illustrate a quantity of pixels (vertical axis) over the values of the color red of the pixels (horizontal axis). As can be seen, several pixels show a darker shade of red, such as for example pixels having values of 120-170 Counts on the horizontal axis, than the majority of pixels, having a value of −180 Counts on the horizontal axis. Thus, when compared to the region of interest illustrated in FIG. 5A, the pixels showing a darker shade of red may clearly be associated with the contaminated or dirty areas 152, in particular with the red colored bloodstain, within the region of interest 128.

Figure 6:
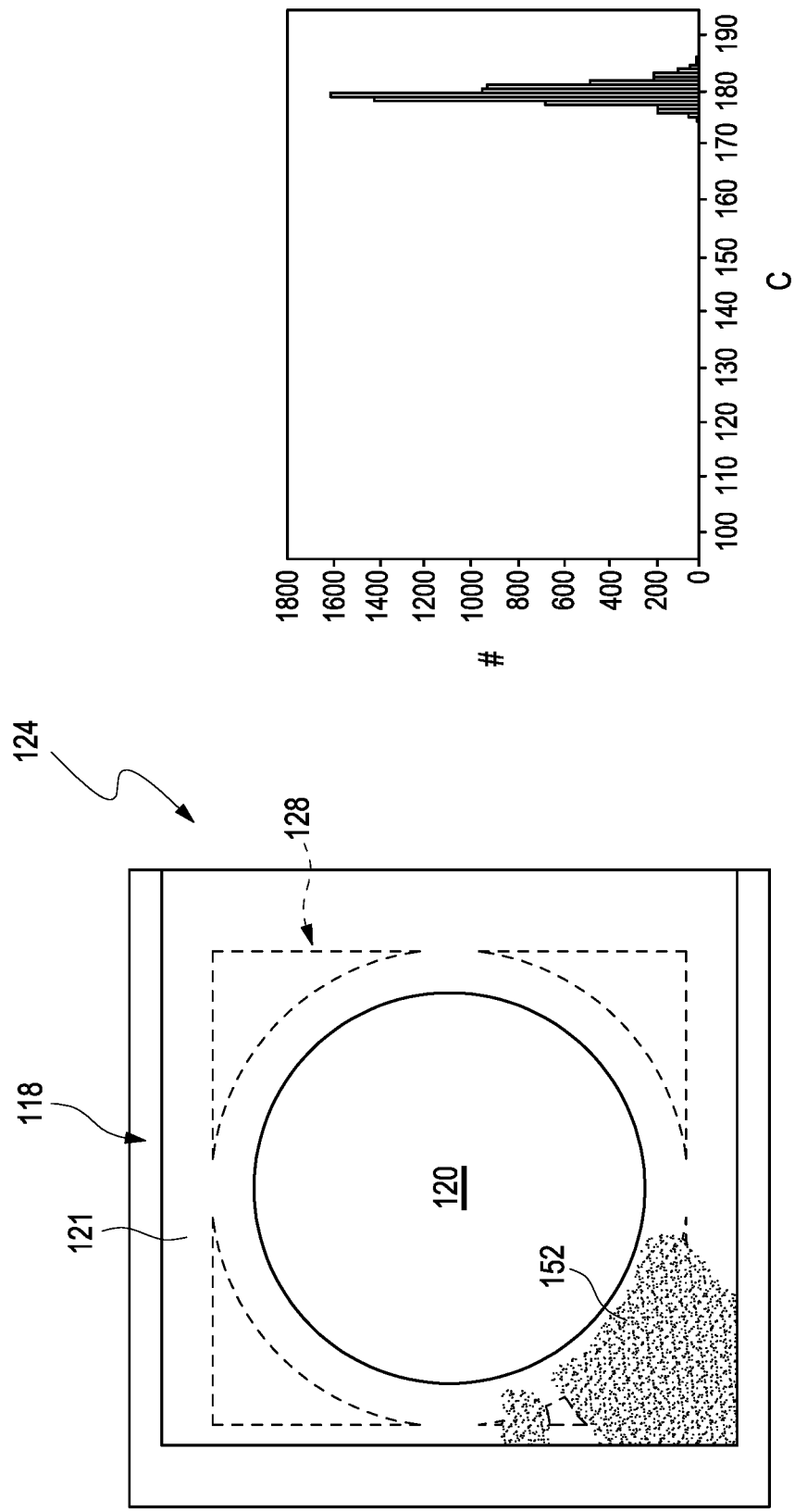

After evaluating the color distribution within the first sub-set of pixels and eliminating outliers in the first sub-set of pixels, the contaminated or dirty areas 152, particularly the red colored bloodstain, within the reference color field 121 may no longer lie within the region of interest 128, as illustrated in FIG. 6A. A histogram corresponding to the region of interest 128 illustrated in FIG. 6A, is shown in FIG. 6B. The histogram, as shown in FIG. 6B, is based on the color coordinates indicating values for the color red, and illustrates the quantity of pixels (vertical axis) over the values of the color red of the pixels (horizontal axis) within the region of interest 128 illustrated in FIG. 6A. As can be seen, the region of interest 128 no longer comprises pixels showing a darker shade of red, such as for example pixels having values of 120-170 Counts on the horizontal axis.

Figure 7:
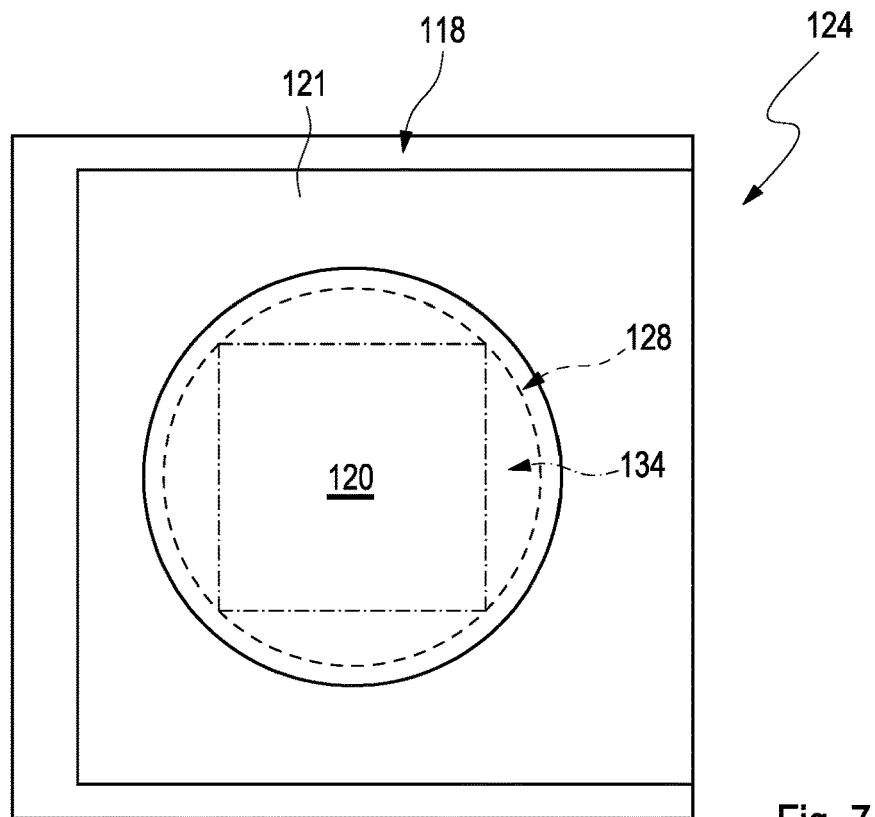
FIGS. 7 and 8 illustrate embodiments of images captured by a mobile device and a determined region of interest as well as a determined sub-region of interest.
Figure 8:
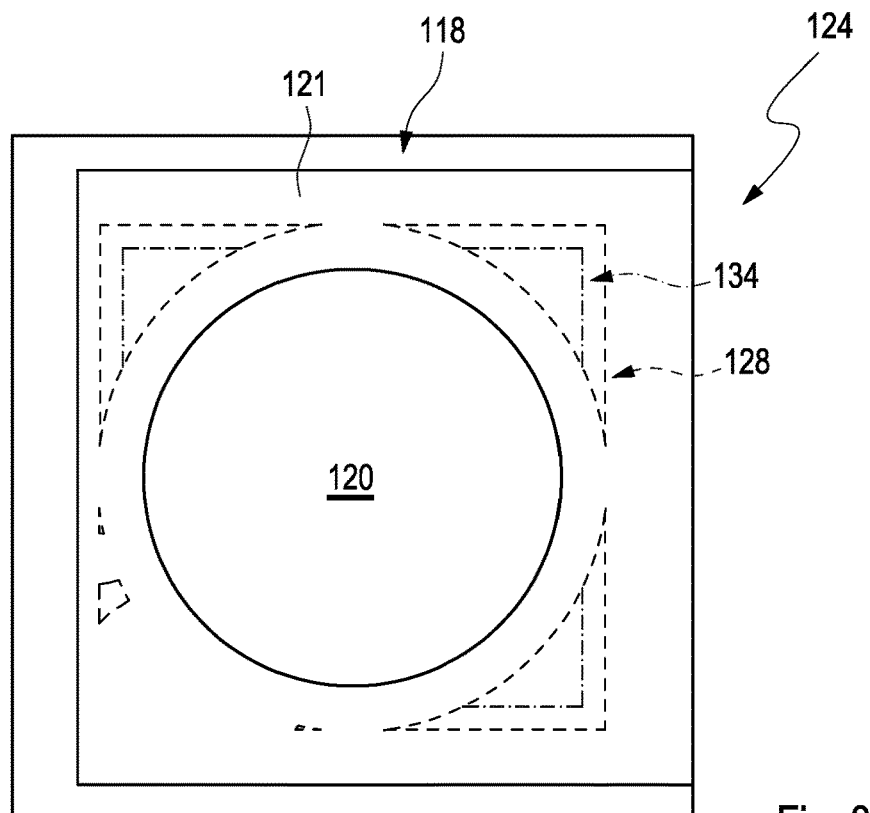

A sub-region of interest 134 may be determined within the region of interest 128. The subregion of interest 134 specifically has a smaller area than the region of interest 128, as shown in the FIGS. 7 and 8. In particular, as illustrated in FIG. 7, the sub-region of interest 134 may for example have a different shape than the region of interest 128.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 step a) providing at least one mobile device having at least one camera
112 mobile device
114 camera
116 step b) providing at least one test strip configured for performing a color-change detection reaction and applying at least one sample to the test strip
118 test strip
120 test field
121 reference color field
122 step c) capturing at least one image of at least a part of the test strip by using the camera
124 image
126 step d) determining at least one region of interest in the image
128 region of interest
130 step e) evaluating a color distribution within the first sub-set of pixels and eliminating outliers in the first sub-set of pixels
132 step f) determining at least one sub-region of interest within the region of interest, the subregion of interest having a smaller area than the region of interest, and associating a second sub-set of pixels with the sub-region of interest
134 sub-region of interest
136 step g) comparing at least one mean value of the color distribution of the first sub-set of pixels and at least one mean value of a color distribution of the second sub-set of pixels and determining thereby at least one item of homogeneity information on a homogeneity of the image
138 branching point
140 first branch
142 second branch 144 step h) if the at least one item of homogeneity information indicates the image being unsuited for performing the analytical measurement, aborting the method for performing the analytical measurement 146 step i) if the at least one item of homogeneity information indicates the image being suited for performing the analytical measurement, evaluating the image and deriving at least one analytical information, specifically at least one item of information on a concentration of at least one analyte in the sample 148 kit
149 processor
150 damages
152 dirty areas

What is claimed is:

1. A method to perform an analytical measurement, comprising:
    a) providing a mobile device having a camera;
    b) providing a test strip configured to perform a color-change detection reaction and applying a sample to a test field of the test strip, the test field containing at least one test chemical for detecting an analyte in the sample;
    c) capturing an image of at least a part of the test strip using the camera, the image comprised of a plurality of pixels;
    d) determining a region of interest in the image and associating a first sub-set of the pixels with the region of interest;
    e) evaluating a color distribution and eliminating outliers in the first sub-set of pixels;
    f) determining a sub-region of interest entirely within the region of interest, the sub-region of interest having a smaller area than the region of interest;
    g) associating a second sub-set of the pixels with the sub-region of interest; and
    h) comparing a mean value of the color distribution of the first sub-set of pixels and a mean value of a color distribution of the second sub-set of pixels and determining thereby homogeneity information of the image;
    wherein the method further comprises
        comparing the number of pixels in the first sub-set of pixels before eliminating the outliers in step e) with the number of pixels in the first sub-set of pixels after eliminating the outliers in step e), wherein, if the number of pixels in the first sub-set of pixels after eliminating the outliers in step e) is smaller than a predetermined percentage of the number of pixels in the first sub-set of pixel before eliminating the outliers in step e), the method to perform the analytical measurement is aborted.

2. The method according to claim 1, further comprising:
    i) when the homogeneity information indicates the image is unsuited to perform the analytical measurement, aborting the method to perform the analytical measurement; and
    ii) when the homogeneity information indicates the image is suited to perform the analytical measurement, evaluating the image to derive analytical information.

3. The method according to claim 1, wherein step h) comprises comparing an absolute value of a difference between the mean value of the color distribution of the first sub-set of pixels and the mean value of the color distribution of the second sub-set of pixels to a threshold value.

4. The method according to claim 3, wherein the homogeneity information indicates the image is suited to perform the analytical measurement when the absolute value of the difference is equal to or smaller than the threshold value.

5. The method according to claim 1, wherein step e) comprises evaluating the color distribution for at least two color coordinates.

6. The method according to claim 1, wherein the test strip has a reference color field, wherein step c) is performed such that the image includes at least a partial image of the test field and at least a partial image of the reference color field, wherein steps d) to h) are performed both for the test field and the reference color field, wherein the reference color field contains at least one white field.

7. The method according to claim 1, wherein step e) uses one or both of a histogram analysis or a percentile analysis of the color distribution to eliminate the outliers.

8. The method according to claim 1, wherein step e) comprises eliminating pixels having a color outside an acceptance interval of $[p1-\Delta p1, p2+\Delta p2]$, with p1 being a lower percentile, p2 being an upper percentile and $\Delta p1$, $\Delta p2$ being positive tolerance ranges.

9. The method according to claim 8, wherein:

$\Delta p1 = f1 \cdot (p2-p1)$, and $\Delta p2 = f2 \cdot (p2-p1)$, with f1, f2 being positive tolerance factors.

10. The method according to claim 1, wherein step d) comprises determining the region of interest by using a pattern recognition method for identifying in the image at least one item selected from the group consisting of: the test field; a part of the test field; a reference color field; and a part of a reference color field.

11. The method according to claim 1, wherein the center of the sub-region of interest coincides with the center of the region of interest.

12. The method to perform an analytical measurement according to claim 1, further comprising comparing the number of pixels within the first sub-set of pixels with a threshold value, thereby determining sufficiency of a size of the region of interest, wherein if the region of interest has an insufficient size, aborting the method to perform the analytical measurement.

13. A non-transitory computer readable medium having stored thereon computer-executable instructions to perform the method according to claim 1.

14. A mobile device to perform an analytical measurement, the mobile device having a camera and a processor, the processor configured to:
    A) cause the camera to capture an image of at least a part of a test strip, wherein the image is comprised of a plurality of pixels;
    B) determine a region of interest in the image and associating a first sub-set of the pixels with the region of interest;
    C) evaluate a color distribution within the first sub-set of pixels and eliminating outliers in the first sub-set of pixels;
    D) determine a sub-region of interest entirely within the region of interest, the sub-region of interest having a smaller area than the region of interest, and associating a second sub-set of the pixels with the sub-region of interest; and
    E) subsequent to step C), compare a mean value of the color distribution of the first sub-set of pixels and a mean value of a color distribution of the second sub-set of pixels and thereby compare homogeneity between the region of interest and the sub-region of interest.

15. A kit to perform an analytical measurement, comprising:
   the mobile device according to claim 14; and
   the test strip configured to perform a color-change detection reaction having a test field containing a test chemical for detecting an analyte in a sample.

16. A method to perform an analytical measurement, comprising:
   a) providing a mobile device having a camera;
   b) providing a test strip configured to perform a color-change detection reaction and applying a sample to a test field of the test strip, the test field containing at least one test chemical for detecting an analyte in the sample;
   c) capturing an image of at least a part of the test strip using the camera, the image comprised of a plurality of pixels;
   d) determining a region of interest in the image and associating a first sub-set of the pixels with the region of interest;
   e) evaluating a color distribution and eliminating outliers in the first sub-set of pixels;
   f) determining a sub-region of interest entirely within the region of interest, the sub-region of interest having a smaller area than the region of interest;
   g) associating a second sub-set of the pixels with the sub-region of interest; and
   h) subsequent to step e), comparing a mean value of the color distribution of the first sub-set of pixels and a mean value of a color distribution of the second sub-set of pixels and thereby comparing homogeneity between the region of interest and the sub-region of interest.

* * * * *